United States Patent
Zhang et al.

(10) Patent No.: US 11,925,498 B2
(45) Date of Patent: Mar. 12, 2024

(54) RECONSTRUCTING IMAGE

(71) Applicant: SHENYANG INTELLIGENT NEUCLEAR MEDICAL TECHNOLOGY CO., LTD., Liaoning (CN)

(72) Inventors: Rumei Zhang, Shanghai (CN); Long Yang, Shanghai (CN); Peng Gao, Shanghai (CN); Guodong Liang, Shanghai (CN); Jun Zhang, Shanghai (CN)

(73) Assignee: Shenyang Intelligent Neuclear Medical Technology Co., Ltd., Shenyang (CN)

( * ) Notice: Subject to any disclaimer, the term of this patent is extended or adjusted under 35 U.S.C. 154(b) by 597 days.

(21) Appl. No.: 17/037,301

(22) Filed: Sep. 29, 2020

(65) Prior Publication Data

US 2021/0093279 A1  Apr. 1, 2021

(30) Foreign Application Priority Data

Sep. 30, 2019 (CN) .......................... 201910945559.4

(51) Int. Cl.
*A61B 6/00* (2006.01)
*A61B 6/03* (2006.01)
*G06T 11/00* (2006.01)

(52) U.S. Cl.
CPC ............ *A61B 6/5205* (2013.01); *A61B 6/037* (2013.01); *A61B 6/4233* (2013.01); *G06T 11/005* (2013.01); *G06T 2210/41* (2013.01)

(58) Field of Classification Search
CPC ..... A61B 6/483; A61B 6/5282; G01T 1/1641; G01T 1/1663; G01T 1/29; G01T 1/2914–2992; G01T 1/36–40
See application file for complete search history.

(56) References Cited

U.S. PATENT DOCUMENTS

2007/0040122 A1* 2/2007 Manjeshwar ......... G01T 1/2985
                                                        250/363.03
2010/0172565 A1* 7/2010 Degenhardt ........... A61B 6/508
                                                        250/363.03
(Continued)

OTHER PUBLICATIONS

Du et al., "A Time-Walk Correction Method for PET Detectors Based on Leading Edge Discriminators," IEEE Transactions on Radiation & Plasma Medical Sciences, 2017, 6 pages.
(Continued)

*Primary Examiner* — Katherine L Fernandez
*Assistant Examiner* — Farouk A Bruce
(74) *Attorney, Agent, or Firm* — Fish & Richardson P.C.

(57) ABSTRACT

The present disclosure relates to reconstructing an image. According to an embodiment of the present disclosure, identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups comprises an energy value less than a preset first energy threshold, the second scan data set comprises one or more second single event data groups and each of the second single event data groups comprises an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence
(Continued)

event data and second coincidence event data which involves coincidence events corresponding to the second scan data set.

16 Claims, 3 Drawing Sheets

(56) References Cited

U.S. PATENT DOCUMENTS

| | | | |
|---|---|---|---|
| 2011/0210255 A1* | 9/2011 | Kim | G01T 1/2985 250/362 |
| 2016/0131774 A1* | 5/2016 | Lage | A61B 6/5217 600/425 |
| 2020/0150293 A1* | 5/2020 | Abbaszadeh | H01L 31/02966 |

OTHER PUBLICATIONS

Wagadarikar et al., "Sensitivity Improvement of Time-of-Flight (ToF) PET Detector Through Recovery of Compton Scattered Annihilation Photons," IEEE Transaction on Nuclear Science, Feb. 2014, 6(1):121-5.

* cited by examiner

RECONSTRUCTING IMAGE

CROSS REFERENCE TO RELATED APPLICATIONS

This application claims priority to Chinese Patent Application No. 201910945559.4 entitled "METHOD AND APPARATUS OF RECONSTRUCTING AN IMAGE, AND CONSOLE DEVICE, PET SYSTEM" and filed on Sep. 30, 2019, the disclosure of which is incorporated herein by reference in its entirety.

TECHNICAL FIELD

The present disclosure relates to the technical field of medical image processing technologies, and more specifically to methods and apparatuses of reconstructing an image, and console devices, PET systems.

BACKGROUND

Positron Emission Tomography (PET) technology is one of the current popular medical imaging technologies. Positron Emission Tomography based on Time of Flight (TOF) (TOF-PET) technology is an important direction for technological development in the field of nuclear medicine. Compared with traditional PET, TOF-PET can provide clearer images.

During the scanning process of the PET system, the PET detector is used to detect high-energy photons emitted from the inside of subject and generate PET scan data based on the detected results. The PET scan data includes not only the single event data corresponding to the coincidence event, but also the single event data corresponding to the intra-crystal Compton scattering event. In a process of reconstructing an image, the single event data corresponding to the intra-crystal Compton scattering event is filtered out according to the energy value, and the single event data corresponding to the coincidence event is used for reconstructing the image. This reduces the total count rate of coincidence events collected by the PET system, resulting in a decrease in the sensitivity of the PET system.

SUMMARY

The present disclosure provides a method and an apparatus of reconstructing an image, and console device, PET system, improving system sensitivity.

In a first aspect, an embodiments of the present disclosure provides a method of reconstructing an image, the method comprising: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups comprises an energy value less than a preset first energy threshold, the second scan data set comprises one or more second single event data groups and each of the second single event data groups comprises an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set.

In a second aspect, an embodiments of the present disclosure provides a console device comprising: an external interface connecting a detector of a PET system, the detector includes a plurality of crystals and corresponding a plurality of photoelectric converters and a processing circuit; a memory storing machine-readable instructions; a processor configured to read the machine-readable instructions on the memory to perform: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups comprises an energy value less than a preset first energy threshold, the second scan data set comprises one or more second single event data groups and each of the second single event data groups comprises an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set; an internal bus connecting the external interface, the processor and the memory.

In a third aspect, an embodiments of the present disclosure provides a PET system comprising: a scanning bed; a detector, the detector includes a plurality of crystals, corresponding a plurality of photoelectric converters, and a processing circuit; wherein, the crystals are used to detect a high-energy photon emitted from an inside of a subject and convert the high-energy photon into an optical signal during a scanning process of the PET system; corresponding a plurality of photoelectric converters, the photoelectric converters are used to convert the optical signal into an electrical signal; a processing circuit for converting the electrical signal into a pulse signal and collecting energy information of the pulse signal; a console device, the console device is used for: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups comprises an energy value less than a preset first energy threshold, the second scan data set comprises one or more second single event data groups and each of the second single event data groups comprises an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set.

In a fourth aspect, an embodiments of the present disclosure provides a non-transitory computer-readable storage medium storing a computer program thereon, wherein the program is executed by a processor to implement: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups comprises an energy value less than a preset first energy threshold, the second scan data set comprises one or more second single event data groups and each of the second single event data groups comprises an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set.

DETAILED DESCRIPTION

Figure 1:
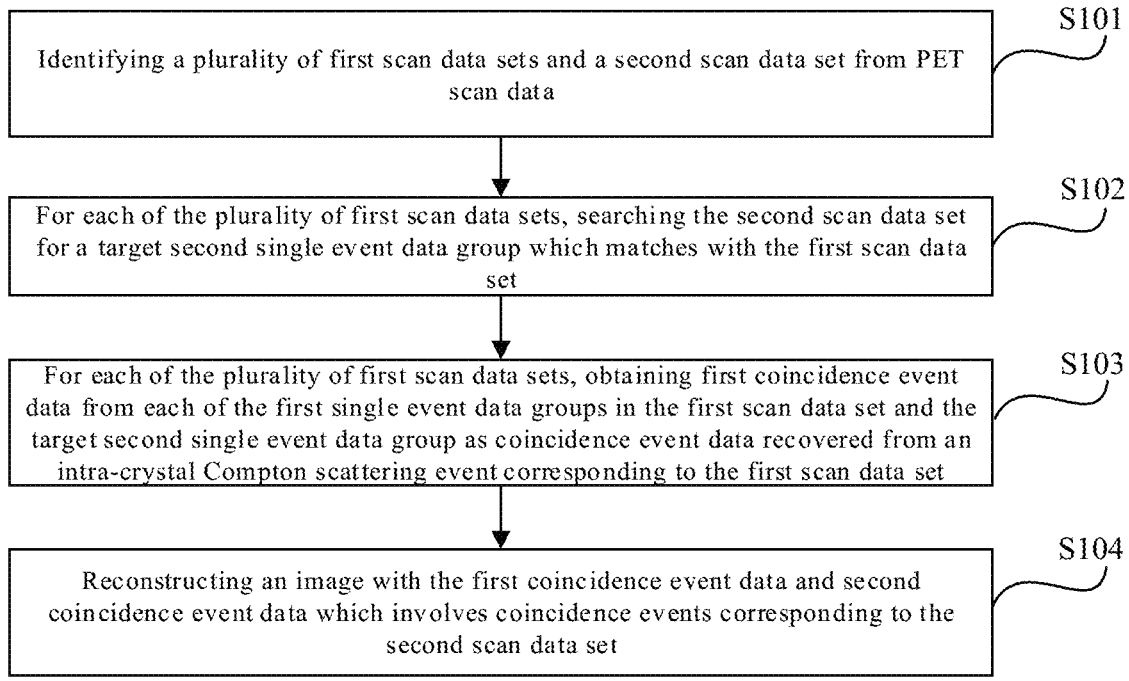
FIG. 1 is a flowchart of a method of reconstructing an image according to an exemplary embodiment of the present disclosure.

PET scan data collected by a PET system includes a plurality of single event data groups. Each of the single event data groups includes energy information, time information and position information. The energy information represents energy of a photon incident into a detector crystal, the time information represents time when the photon is incident into the detector crystal, and the position information represents a position of the detector crystal on which the photon is incident. In the disclosure, for the convenience of description, a single event data group is sometimes referred to as single event data for short, so as to emphasize that the group of data including energy, time, position and other information corresponds to a single event.

During a process of performing PET scanning on a subject, when an annihilation event occurs in a target area for the subject, two photons with the same energy and opposite moving directions can be generated. The two photons respectively reach detector crystals that form a 180-degree angle to each other and are captured by the detector to generate two single event data groups. An annihilation position can be determined by performing coincidence processing on the two single event data groups, thereby generating a coincidence event count.

If one photon of the two photons arrives at the detector crystal in an original direction (here the original direction refers to the movement direction of the photon generated in the annihilation event), the other photon undergoes intra-crystal Compton scattering during the movement, the other photon will generate a plurality of scattered photons after being scattered. The plurality of scattered photons are respectively incident into the detector crystals and captured by the detector to generate a plurality of single event data sets. Each scattered photon corresponds to a single event, that is, corresponds to a single event data set. An original coincidence event can be restored based on single event data related to an intra-crystal Compton scattering event, thereby increasing the coincidence event count.

In the related art, during a process of reconstructing an image using PET scan data, the PET scan data is first filtered according to a preset energy threshold. The single event data whose energy value exceeds the preset energy threshold is passed and used for reconstructing an image, while the single event data whose energy value does not exceed the preset energy threshold is filtered out. Since the energy of the scattered photon is less than the energy of the unscattered photon, in the related technology, the single event data related to an intra-crystal Compton scattering event will be filtered out, so that the coincidence event count is reduced and the PET system sensitivity is reduced.

The method of reconstructing an image provided in the present disclosure can restore an intra-crystal Compton scattering event to a coincidence event, thereby increasing the coincidence event count and improving the sensitivity of the PET system.

The method of reconstructing an image provided in the present disclosure is described below through exemplary embodiments.

FIG. 1 is a flowchart of a method of reconstructing an image according to an exemplary embodiment of the present disclosure. The method of reconstructing an image can be used for image reconstruction of PET scan data. As shown in FIG. 1, the method of reconstructing an image may include step S101 to step S104.

S101, a plurality of first scan data sets and a second scan data set are identified from PET scan data. Wherein, each of the first scan data sets corresponds to an intra-crystal Compton scattering event occurred in a plurality of crystals of a detector and includes two or more first single event data groups, and each of the first single event data groups includes an energy value less than a preset first energy threshold, the second scan data set includes one or more second single event data groups and each of the second single event data groups includes an energy value exceed a preset second energy threshold, the first energy threshold is not greater than the second energy threshold.

S102, for each of the plurality of first scan data sets, the second scan data set is searched for a target second single event data group which matches with the first scan data set.

S103, for each of the plurality of first scan data sets, first coincidence event data is obtained from each of the first single event data groups in the first scan data set and the target second single event data group which matches with the first scan data set as coincidence event data recovered from an intra-crystal Compton scattering event corresponding to the first scan data set.

S104, an image is reconstructed with the first coincidence event data and second coincidence event data which involves coincidence events corresponding to the second scan data set.

The PET scan data includes all single event data groups collected during the PET scanning process.

Intra-crystal Compton scattering refers to Compton scattering that occurs in a crystal. Each intra-crystal Compton scattering event corresponds to two or more single events. Therefore, in step S101, a first scan data set corresponding to an intra-crystal Compton scattering event includes two or more first single event data groups.

In step S101, the second scan data set refers to a set of single event data groups which pass energy value filter in the above related technology.

Figure 5A:
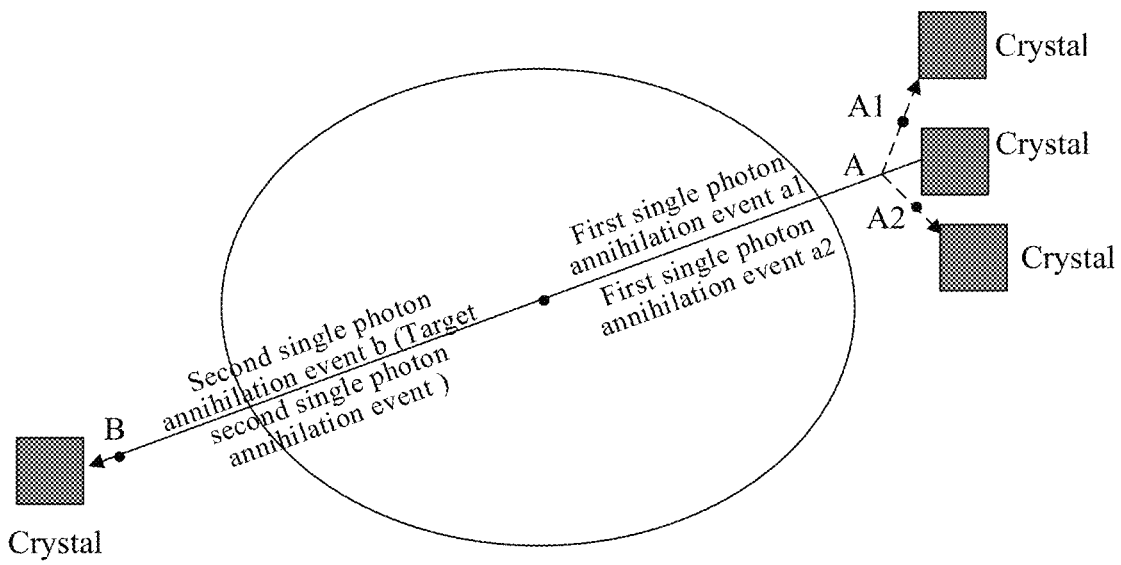
FIGS. 5A and 5B are schematic diagrams of single events according to an exemplary embodiment of the present disclosure.

For example, as illustrated in FIG. 5A, in an annihilation event, two photons with the same energy and opposite moving directions can be generated: photon A and photon B. The incident of photon B into a detector crystal in the original direction is recorded as single event b; photon A undergoes intra-crystal Compton scattering during the movement and generates two scattered photons: photon A1 and photon A2. The incident of photon A1 into a detector crystal is recorded as single event a1, and the incident of photon A2 into a detector crystal is recorded as single event a2.

Figure 5B:
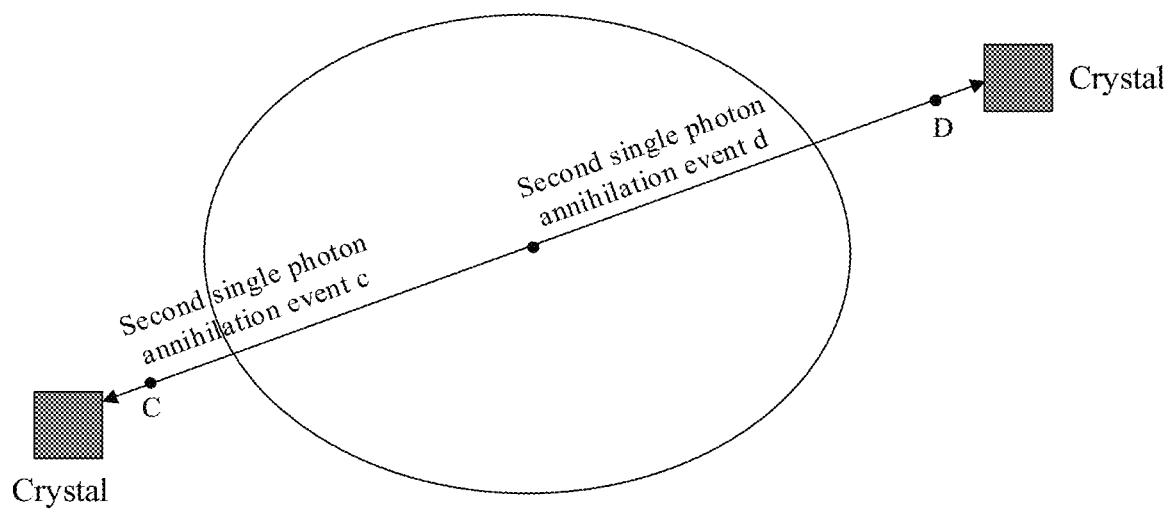

In another annihilation event, e.g., as illustrated in FIG. 5B, two photons with the same energy and opposite moving directions can be generated: photon C and photon D. The incident of photon C into a detector crystal in the original direction is recorded as single event c, and the incident of photon D into a detector crystal in the original direction is recorded as single event d.

Wherein, since single event a1 and single event a2 correspond to the same intra-crystal Compton scattering event, the data of single event a1 and the data of single event a2 constitute the first scan data set; in addition, the data of single event b, the data of single event c and the data of single event d constitute the second scan data set.

In an exemplary embodiment, step S101 can include: for each single event data group in the PET scan data, searching the PET scan data for a target single event data group which matches with the single event data group. In an exemplary embodiment, the target single event data group satisfies all the following conditions: a distance between a first spatial position indicated by spatial position information in the target single event data group and a second spatial position indicated by spatial position information in the single event data group is less than a preset distance threshold; difference between first time indicated by time information in the target single event data group and second time indicated by time information in the single event data group is less than a preset time threshold; a first energy value in the target single event data group and a second energy value in the single event data group are both smaller than the preset first energy threshold.

If the target single event data group is searched out, it is can be determined that the target single event data group and the single event data group constitute a first scan data set corresponding to the same scattering event, the same scattering event is the same intra-crystal Compton scattering event.

In this embodiment, the first scan data set corresponding to the same intra-crystal Compton scattering event is identified by utilizing the characteristics of close spatial position (for example, the spatial straight line span is within 6 crystals), small time intervals (for example, time interval is no more than 2-3 times the system time resolution) between a plurality of single events corresponding to a plurality scattered photons involved in the same intra-crystal Compton scattering event and low energy (for example, less than 435 kev), thus providing a basis for restoring an intra-crystal Compton scattering event to a coincidence event. In addition, in this embodiment, an intra-phantom Compton scattering event or other normal events can be avoided from being mistaken as intra-crystal Compton scattering events by utilizing the above conditions, thereby improving the identification accuracy.

Each first single event data group in each first scan data set can be marked after identifying a first scan data set corresponding to an intra-crystal Compton scattering event through step S101. The mark may be used to indicate that the first single event data group is the data corresponding to an intra-crystal Compton scattering event.

In an exemplary embodiment, before step S101, the method may further include: performing system time correction on the collected PET scan data to obtain corrected PET scan data.

In an exemplary embodiment, identifying each first scan data set and second scan data set from the collected PET scan data includes: identifying each first scan data set corresponding to an intra-crystal Compton scattering event and the second scan data set from the corrected PET scan data.

In this embodiment, a time error caused by factors such as the system global clock or installation can be compensated by performing system time correction on the PET scan data, thereby improving data accuracy.

In an exemplary embodiment, step S102 can be implemented in the following manner: for each first scan data set, single event data groups in the first scan data set and the second scan data set are sorted according to time; in the second scan data set, the second single event data group that is in the same time window as all first single event data groups in the first scan data set is searched for; the found second single event data group is taken as a target second single event data group which matches with the first scan data set. Wherein, the width of the time window can be a preset width.

For example. The above single event a1, single event a2, single event b, single event c, and single event d are sorted according to the time indicated by the time information in the single event data group, and time window 1 within which both the single event a1 and the single event a2 are occurred is found. Assuming that the single event b is occurred within the time window 1, the single event c and the single event d are occurred outside the time window 1, then it is determined that the data of single event b is a target second single event data group which matches with the data of single event a1 and single event a2.

In an exemplary embodiment, step S103 may include: obtaining an initial reconstructed image by reconstructing an image according to scan data in the PET scan data which involves coincidence events; performing, for each of the first single event data groups in each first scan data set, a coincidence processing on the first single event data group and the target second single event data group which matches with the first scan data set, so to obtain a plurality of Lines of Response (LORs); determining, for each of the LORs, a Time of Flight (TOF) kernel function so to obtain a plurality of TOF kernel functions; performing, for each of the TOF kernel functions, line integration with the TOF kernel function and pixel values in the initial reconstructed image so to obtain a probability value of corresponding LOR for the TOF kernel function; determining the first coincidence event data as including a first single event data group corresponding to the LOR with a largest probability value and the target second single event data group.

In this embodiment, the scan data in the PET scan data which involves coincidence events is the second single event data group that can form the coincidence even in the second scan data.

Take the above single event a1, single event a2, single event b, single event c, and single event d as examples. Wherein, the data of single event a1 and the data of single event a2 belong to the first scan data set; the data of single event b, the data of single event c, and the data of single event d belong to the second scan data set, but the data of single event b cannot form a coincidence event with other single event data groups in the second scan data set, while the data of single event c and the data of single event d can form a coincidence event. Therefore, the data of single event c and the data of single event d are the scan data corresponding to the coincidence event, and constitute the second coincidence event data; while the data of single event b is not the scan data corresponding to the coincidence event, that is, the target second single event data group; and the data of single event b and the data of single event a1 or the data of single event a2 constitute the first coincidence event data.

The initial reconstructed image is obtained by reconstructing an image according to the scan data in the PET scan data which involves coincidence events. The initial reconstructed image is also an image obtained by reconstructing an image according to the aforementioned related technology.

For each of the first single event data groups in each first scan data set, a coincidence processing is performed on the first single event data group and the target second single event data group which matches with the first scan data set, that is, for each first single event data group corresponding to a scattered photon, a coincidence processing is performed on the first single event data group and the target second single event data group.

Take the first scan data set composed of the data of single event a1 and the data of single event a2 as an example. The data of single event b is the target second single event data group which matches with the data of single event a1 and the data of single event a2. LOR p1 is obtained by performing a coincidence processing on the data of single event b and the data of single event a1, and LOR p2 is obtained by performing a coincidence processing on the data of single event b and the data of single event a2.

Suppose that in an annihilation event, one generated photon is incident into crystal C1 in the original direction, and the other photon is incident into crystal C2, crystal C3, and crystal C4 after undergoing intra-crystal Compton scattering. The obtained three LORs can be shown in FIG. 2.

Figure 2:
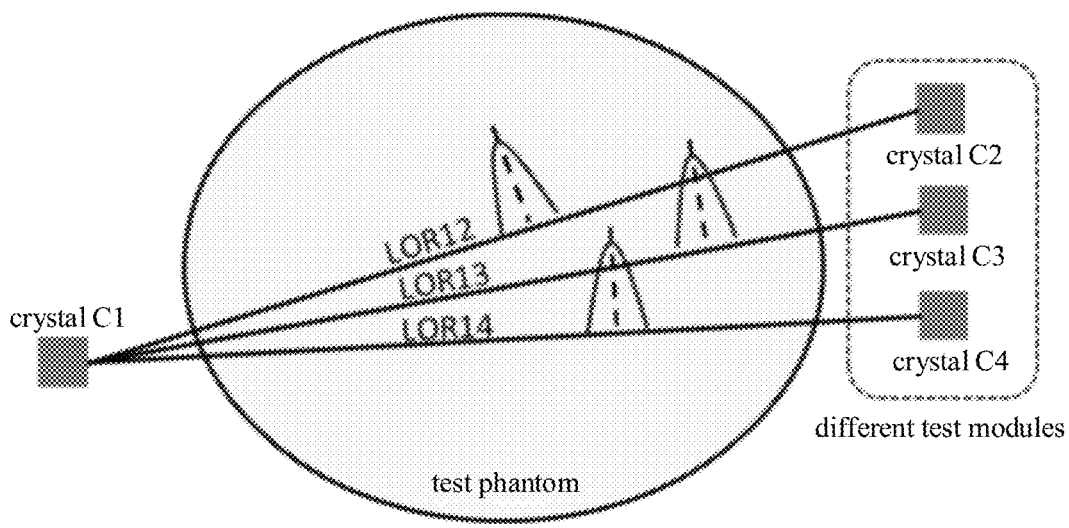
FIG. 2 is a diagram for a plurality of lines of response (LORs) formed by an intra-crystal Compton scattering event according to an exemplary embodiment of the present disclosure.

FIG. 2 is a diagram for a plurality of LORs formed by an intra-crystal Compton scattering event according to an exemplary embodiment of the present disclosure. Referring to FIG. 2, LOR 12 passes through crystal C1 and crystal C2, LOR 13 passes through crystal C1 and crystal C3, and LOR 14 passes through crystal C1 and crystal C4. The crystal here can represent a position indicated by the position information in the corresponding single event data group. For example, crystal C2 represents a position indicated by the position information in a single event data group corresponding to a scattered photon. In FIG. 2, the test phantom is the subject.

In this embodiment, the TOF kernel function may be a Gaussian TOF kernel function formed according to the coincidence time difference.

In this embodiment, a probability value of a LOR is equal to a line integration result of a TOF kernel function corresponding to the LOR and pixel values in the initial reconstructed image. For example, in a range of ±3σ, the TOF kernel function is integrated with the pixel values in the initial reconstructed image, and the obtained result is the probability value of the LOR. The first coincidence event data may be determined as including a first single event data group corresponding to the LOR with a largest probability value and the target second single event data group. And the first coincidence event data is used for reconstructing an image together with second coincidence event data which involves coincidence events corresponding to the second scan data set.

In this embodiment, a probability value of a LOR is determined by performing line integration with a TOF kernel function corresponding to the LOR and pixel values in the initial reconstructed image, and then the corresponding LOR for a coincidence event which recovered from a scattering event is determined based on the probability value of the LOR, such that the corresponding LOR for the coincidence event which recovered from an intra-crystal Compton scattering event can be accurately spatially positioned. And the accuracy of spatial position for the LOR is improved, thus contributing to improving the image quality of the reconstructed image.

In an exemplary embodiment, before step S103, the method may further include: performing time walk error correction on all first scan data sets and the second scan data set in the PET scan data. Correspondingly, step S103 may include: obtaining first coincidence event data from time-walk-error corrected first single event data groups in the first scan data set and time-walk-error corrected target second single event data group as coincidence event data recovered from an intra-crystal Compton scattering event; step S104 may include: an image is reconstructed with the first coincidence event data and time-walk-error corrected second coincidence event data in the second scan data set.

For example, for the above data of single event a1 and the data of single event a2 belonging to the first scan data set, and the data of single event b, the data of single event c, and the data of single event d belonging to the second scan data set, before using the data of single event a1, the data of single event a2 and the data of single event b for scattering event recovery, the data of single event a1, the data of single event a2, the data of single event b, the data of single event c, and the data of single event d can be performed time walk error correction.

In an exemplary embodiment, performing time walk error correction on all first scan data sets and the second scan data set in the PET scan data may include: for each single event data group of all first scan data sets and the second scan data set in the PET scan data, obtaining an energy to time-walk-error correspondence of a crystal corresponding to the single event data group with respect to a reference crystal; obtaining a target time walk error corresponding to a target energy value in the single event data group based on the energy to time-walk-error correspondence; determining a sum of a time value in the single event data group and the target time walk error; updating the time value in the single event data group to a value of the sum.

In this embodiment, the crystal refers to the detector crystal. For each crystal, the energy to time-walk-error correspondence between the crystal with the reference crystal can be obtained in the following manner.

Assuming that there is a reference crystal M (also called a reference detector crystal) and a to-be-tested crystal N (also called a to-be-tested detector crystal), the reference crystal M is used to measure the time walk error for the to-be-tested crystal N.

In a first step, all single event data for the reference crystal M and the to-be-tested crystal N is collected, and a single event with the energy of the reference crystal M at 511 kev±DE (in order to reduce the influence of time walk for the reference crystal M on the to-be-tested crystal N, DE is very small, for example, DE is 2.5 kev) is selected as a reference single event.

In a second step, the collected energy of a series of single events for the to-be-tested crystal N is divided into blocks, and the energy blocks are respectively performed coincidence processing with the reference single event. When the energy blocks and the reference single event are in coincidence processing, a coincidence time Gaussian distribution map with respect to the time difference is formed.

In a third step, a midpoint of the Gaussian time distribution formed by performing coincidence processing on the energy blocks (511 kev±DE) in the to-be-tested crystal N and the reference single event is taken as a reference point, a midpoint of the Gaussian coincidence time formed by other energy blocks is subtracted from the reference point to obtain time difference, and the time difference is stored.

In a fourth step, a series of energy blocks in the to-be-tested crystal N can be performed coincidence processing with the reference single event to form a series of Gaussian distribution time midpoints, and then form a table. The data in the table can be fitted to obtain an energy-time walk error fitting formula.

The energy-time walk error fitting formula can be used to represent an energy to time-walk-error correspondence of the crystal with respect to the reference crystal. When collecting the single event for the to-be-tested crystal N, a time walk error can be obtained according to the energy of the single event for the to-be-tested crystal N using the above energy-time walk error fitting formula, and a time value of the single event for the to-be-tested crystal N is added to the obtained time walk error to obtain a time value of the single event after time walk error correction.

In this embodiment, the method of time walk error correction can be performed in various known manners in the related art, and will not be repeated here.

In this embodiment, the time walk error correction is performed on the single event data group, especially the time value in the single event data group, thereby improving the accuracy of the data, and further improving the image quality of the reconstructed image.

In this embodiment, the energy to time-walk-error correspondence of the crystal is preset in the system.

According to the method of reconstructing an image provided by an embodiment of the present disclosure, a plurality of first scan data sets and a second scan data set are identified from PET scan data, wherein each of the first scan data sets corresponds to an intra-crystal Compton scattering event occurred in a plurality of crystals of a detector and includes first single event data groups whose energy values are less than a preset first energy threshold, the second scan data set includes second single event data groups whose energy values exceed a preset second energy threshold; for each of the plurality of first scan data sets: the second scan data set is searched for a target second single event data group which matches with the first scan data set; first coincidence event data is obtained from each of the first single event data groups in the first scan data set and the target second single event data group which matches with the first scan data set as coincidence event data recovered from an intra-crystal Compton scattering event corresponding to the first scan data set; an image is reconstructed with the first coincidence event data and second coincidence event data which involves coincidence events corresponding to the second scan data set to obtain an reconstructed image. The intra-crystal Compton scattering event is restored to a coincidence event, which increases the energy value of the scattering region and improves the system sensitivity.

Based on the foregoing method embodiments, the present disclosure also provides corresponding apparatus, device, system, and storage medium embodiments. For detailed implementation of the apparatus, device, system, and storage medium embodiments of the present disclosure, please refer to the corresponding descriptions in the foregoing method embodiments.

Figure 3:
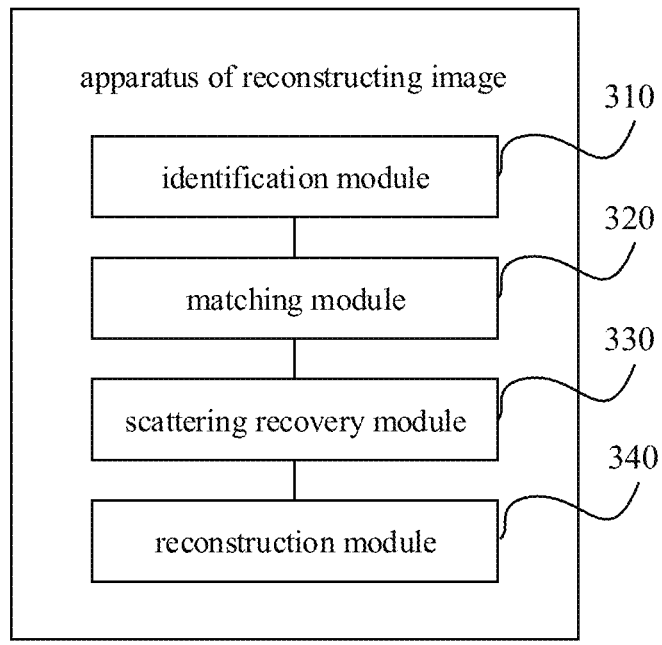
FIG. 3 is a functional block diagram of an apparatus of reconstructing an image according to an exemplary embodiment of the present disclosure.

FIG. 3 is a functional block diagram of an apparatus of reconstructing an image according to an exemplary embodiment of the present disclosure. As shown in FIG. 3, in this embodiment, the apparatus of reconstructing an image may include: an identification module 310, a matching module 320, a scattering recovery module 330, and a reconstruction module 340.

The identification module 310 is configured to identify a plurality of first scan data sets and a second scan data set from PET scan data, wherein, each of the first scan data sets corresponds to an intra-crystal Compton scattering event occurred in a plurality of crystals of a detector and includes two or more first single event data groups, and each of the first single event data groups includes an energy value less than a preset first energy threshold, the second scan data set includes one or more second single event data groups and each of the second single event data groups includes an energy value exceed a preset second energy threshold.

The matching module 320 is configured to, for each of the plurality of first scan data sets, search the second scan data set for a target second single event data group which matches with the first scan data set.

The scattering recovery module 330 is configured to, for each of the plurality of first scan data sets, obtain first coincidence event data from each of the first single event data groups in the first scan data set and the target second single event data group as coincidence event data recovered from an intra-crystal Compton scattering event corresponding to the first scan data set.

The reconstruction module 340 is configured to reconstruct an image with the first coincidence event data and second coincidence event data which involves coincidence events corresponding to the second scan data set.

In an exemplary embodiment, the identification module 310 may be configured to: for each single event data group in the PET scan data, search the PET scan data for a target single event data group which matches with the single event data group, wherein the target single event data group satisfies following conditions: a distance between a first spatial position indicated by spatial position information in the target single event data group and a second spatial position indicated by the single event data group is less than a preset distance threshold; difference between first time indicated by time information in the target single event data group and second time indicated by the single event data group is less than a preset time threshold; a first energy value in the target single event data group and a second energy value in the single event data group are both smaller than the first energy threshold; if the target single event data group is searched out, determine that the target single event data group and the single event data group belong to a first scan data set corresponding to the same intra-crystal Compton scattering event.

In an exemplary embodiment, the scattering recovery module 330 may be configured to: obtain an initial reconstructed image by reconstructing an image according to scan data in the PET scan data which involves coincidence events; perform, for each of the first single event data groups in each first scan data set, a coincidence processing on the first single event data group and the target second single event data group, so to obtain a plurality of LORs; determine, for each of the LORs, a TOF kernel function so to obtain a plurality of TOF kernel functions; perform, for each of the TOF kernel functions, line integration with the TOF kernel function and pixel values in the initial reconstructed image so to obtain a probability value of corresponding LOR for the TOF kernel function; determine the first coincidence event data as including a first single event data group corresponding to the LOR with a largest probability value and the target second single event data group.

In an exemplary embodiment, the apparatus of reconstructing an image may further include a walk error correction module configured to perform time walk error correction on all first scan data sets and the second scan data set in the PET scan data.

The scattering recovery module 330 is configured to: obtain first coincidence event data from time-walk-error corrected first single event data groups in the first scan data set and time-walk-error corrected target second single event data group as coincidence event data recovered from an intra-crystal Compton scattering event.

The reconstruction module 340 is configured to: reconstruct an image with the first coincidence event data and time-walk-error corrected second coincidence event data in the second scan data set.

In an exemplary embodiment, the walk error correction module is configured to: for each single event data group of all first scan data sets and the second scan data set in the PET scan data, obtain an energy to time-walk-error correspondence of a crystal corresponding to the single event data group with respect to a reference crystal; obtain a target time walk error corresponding to a target energy value in the single event data group based on the energy to time-walk-error correspondence; determine a sum of a time value in the single event data group and the target time walk error; update the time value in the single event data group to a value of the sum.

In an exemplary embodiment, the apparatus of reconstructing an image may further include a system correction module configured to perform system time correction on the collected PET scan data to obtain corrected PET scan data.

The identification module 310 may be configured to identify each first scan data set corresponding to an intra-crystal Compton scattering event and the second scan data set from the corrected PET scan data.

Figure 4:
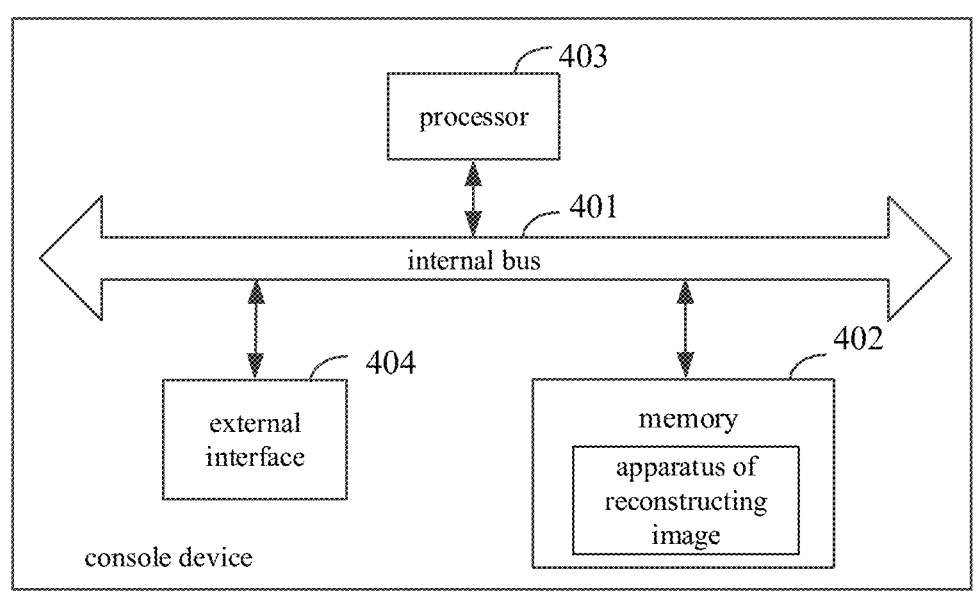
FIG. 4 is a hardware structure diagram of a console device according to an exemplary embodiment of the present disclosure.

The embodiment of the present disclosure also provides a console device. FIG. 4 is a hardware structure diagram of a console device according to an exemplary embodiment of the present disclosure. As shown in FIG. 4, the console device includes: an internal bus 401, and a memory 402, a processor 403, and an external interface 404 connected through the internal bus 401.

The external interface 404 is used to connect a detector of a PET system, the detector includes a plurality of scintillation crystals and corresponding a plurality of photoelectric converters and a processing circuit; the memory is used to store machine-readable instructions.

The processor 403 is configured to read the machine-readable instructions on the memory 402 and perform the instructions to implement: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups includes an energy value less than a preset first energy threshold, the second scan data set includes one or more second single event data groups and each of the second single event data groups includes an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set.

In an exemplary embodiment, identifying the first scan data set corresponding an intra-crystal Compton scattering event from the PET scan data includes: for each single event data group in the PET scan data, searching the PET scan data for a target single event data group which matches with the single event data group, wherein the target single event data group satisfies following conditions: a distance between a first spatial position indicated by spatial position information in the target single event data group and a second spatial position indicated by the single event data group is less than a preset distance threshold; difference between first time indicated by time information in the target single event data group and second time indicated by the single event data group is less than a preset time threshold; a first energy value in the target single event data group and a second energy value in the single event data group are both smaller than the first energy threshold; if the target single event data group is searched out, determining that the target single event data group and the single event data group belong to a first scan data set corresponding to the same intra-crystal Compton scattering event.

In an exemplary embodiment, obtaining first coincidence event data from each of the first single event data groups in the first scan data set and the target second single event data group as coincidence event data recovered from an intra-crystal Compton scattering event corresponding to the first scan data set includes: obtaining an initial reconstructed image by reconstructing an image according to scan data in the PET scan data which involves coincidence events; performing, for each of the first single event data groups in each first scan data set, a coincidence processing on the first single event data group and the target second single event data group, so to obtain a plurality of LORs; determining, for each of the LORs, a TOF kernel function so to obtain a plurality of TOF kernel functions; performing, for each of the TOF kernel functions, line integration with the TOF kernel function and pixel values in the initial reconstructed image so to obtain a probability value of corresponding LOR for the TOF kernel function; determining the first coincidence event data as including a first single event data group corresponding to the LOR with a largest probability value and the target second single event data group.

In an exemplary embodiment, before obtaining first coincidence event data from each of the first single event data groups in the first scan data set and the target second single event data group as coincidence event data recovered from an intra-crystal Compton scattering event corresponding to the first scan data set, the processor 403 may be further configured to implement: performing time walk error correction on all first scan data sets and the second scan data set in the PET scan data.

Correspondingly, obtaining first coincidence event data from each of the first single event data groups in the first scan data set and the target second single event data group as coincidence event data recovered from an intra-crystal Compton scattering event corresponding to the first scan data set includes: obtaining first coincidence event data from time-walk-error corrected first single event data groups in the first scan data set and time-walk-error corrected target second single event data group as coincidence event data recovered from an intra-crystal Compton scattering event.

And correspondingly, reconstructing an image with the first coincidence event data and the second coincidence event data includes: reconstructing an image with the first coincidence event data and time-walk-error corrected second coincidence event data in the second scan data set.

In an exemplary embodiment, performing time walk error correction on all first scan data sets and the second scan data set in the PET scan data may include: for each single event data group of all first scan data sets and the second scan data set in the PET scan data, obtaining an energy to time-walk-error correspondence of a crystal corresponding to the single event data group with respect to a reference crystal; obtaining a target time walk error corresponding to a target energy value in the single event data group based on the energy to time-walk-error correspondence; determining a sum of a time value in the single event data group and the target time walk error; updating the time value in the single event data group to a value of the sum.

In an exemplary embodiment, before identifying each first scan data set and a second scan data set from the collected PET scan data, the processor 403 may be further configured to implement: performing system time correction on the collected PET scan data to obtain corrected PET scan data.

In an exemplary embodiment, identifying each first scan data set and the second scan data set from the collected PET scan data includes: identifying each first scan data set corresponding to an intra-crystal Compton scattering event and the second scan data set from the corrected PET scan data.

The embodiment of the present disclosure also provides a PET system including a detector, a scanning bed and a console device.

The detector includes a plurality of scintillation crystals, corresponding a plurality of photoelectric converters, and a processing circuit. Wherein, the scintillation crystals are used to detect a high-energy photon emitted from an inside of a subject and convert the high-energy photon into an optical signal during a scanning process of the PET system; the photoelectric converters are used to convert the optical signal into an electrical signal; the processing circuit for converting the electrical signal into a pulse signal and collecting energy information of the pulse signal.

The console device is used for: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups includes an energy value less than a preset first energy threshold, the second scan data set includes one or more second single event data groups and each of the second single event data groups includes an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set.

The embodiment of the present disclosure also provides a non-transitory computer-readable storage medium storing a computer program thereon, wherein the program is executed by a processor to implement: identifying a plurality of first scan data sets and a second scan data set from PET scan data, wherein each of the first scan data sets corresponds to an intra-crystal Compton scattering event occurred in a plurality of crystals of a detector and includes two or more first single event data groups, and each of the first single event data groups includes an energy value less than a preset first energy threshold, the second scan data set includes one or more second single event data groups and each of the second single event data groups includes an energy value exceed a preset second energy threshold; for each of the plurality of first scan data sets: searching the second scan data set for a target second single event data group which matches with the first scan data set; obtaining first coincidence event data from each of the first single event data groups in the first scan data set and the target second single event data group as coincidence event data recovered from an intra-crystal Compton scattering event corresponding to the first scan data set; reconstructing an image with the first coincidence event data and second coincidence event data which involves coincidence events corresponding to the second scan data set.

In an exemplary embodiment, identifying the first scan data set corresponding an intra-crystal Compton scattering event from the PET scan data includes: for each single event data group in the PET scan data, searching the PET scan data for a target single event data group which matches with the single event data group, wherein the target single event data group satisfies following conditions: a distance between a first spatial position indicated by spatial position information in the target single event data group and a second spatial position indicated by the single event data group is less than a preset distance threshold; difference between first time indicated by time information in the target single event data group and second time indicated by the single event data group is less than a preset time threshold; a first energy value in the target single event data group and a second energy value in the single event data group are both smaller than the first energy threshold; if the target single event data group is searched out, determining that the target single event data group and the single event data group belong to a first scan data set corresponding to the same intra-crystal Compton scattering event.

In an exemplary embodiment, obtaining first coincidence event data from each of the first single event data groups in the first scan data set and the target second single event data group as coincidence event data recovered from an intra-crystal Compton scattering event corresponding to the first scan data set includes: obtaining an initial reconstructed image by reconstructing an image according to scan data in the PET scan data which involves coincidence events; performing, for each of the first single event data groups in each first scan data set, a coincidence processing on the first single event data group and the target second single event data group, so to obtain a plurality of LORs; determining, for each of the LORs, a TOF kernel function so to obtain a plurality of TOF kernel functions; performing, for each of the TOF kernel functions, line integration with the TOF kernel function and pixel values in the initial reconstructed image so to obtain a probability value of corresponding LOR for the TOF kernel function; determining the first coincidence event data as including a first single event data group corresponding to the LOR with a largest probability value and the target second single event data group.

In an exemplary embodiment, before obtaining first coincidence event data from each of the first single event data groups in the first scan data set and the target second single event data group as coincidence event data recovered from an intra-crystal Compton scattering event corresponding to the first scan data set, the processor may be further configured to implement: performing time walk error correction on all first scan data sets and the second scan data set in the PET scan data.

Correspondingly, obtaining first coincidence event data from each of the first single event data groups in the first scan data set and the target second single event data group as coincidence event data recovered from an intra-crystal Compton scattering event corresponding to the first scan data set includes: obtaining first coincidence event data from time-walk-error corrected first single event data groups in the first scan data set and time-walk-error corrected target second single event data group as coincidence event data recovered from an intra-crystal Compton scattering event.

And correspondingly, reconstructing an image with the first coincidence event data and the second coincidence event data includes: reconstructing an image with the first coincidence event data and time-walk-error corrected second coincidence event data in the second scan data set.

In an exemplary embodiment, performing time walk error correction on all first scan data sets and the second scan data set in the PET scan data may include: for each single event data group of all first scan data sets and the second scan data set in the PET scan data, obtaining an energy to time-walk-error correspondence of a crystal corresponding to the single event data group with respect to a reference crystal; obtaining a target time walk error corresponding to a target energy value in the single event data group based on the energy to time-walk-error correspondence; determining a sum of a time value in the single event data group and the target time walk error; updating the time value in the single event data group to a value of the sum.

In an exemplary embodiment, before identifying each first scan data set and a second scan data set from the collected PET scan data, the processor may be further configured to implement: performing system time correction on the collected PET scan data to obtain corrected PET scan data.

In an exemplary embodiment, identifying each first scan data set and the second scan data set from the collected PET scan data includes: identifying each first scan data set corresponding to an intra-crystal Compton scattering event and the second scan data set from the corrected PET scan data.

For the apparatus and device examples, since they basically correspond to the method example, reference may be made to the partial description of the method example. The apparatus examples described above are merely illustrative, wherein the modules/units described as separate components may or may not be physically separate, and the components displayed as modules/units may or may not be physical modules/units, that is, may be located at one place, or can be distributed to multiple network modules/units. Some or all the modules/units may be selected according to actual needs to achieve the objectives of the present disclosure. It can be understood and implemented by those of ordinary skill in the art without any creative effort.

The terms used in the present disclosure are for the purpose of describing a particular example only, and are not intended to limit the present disclosure. The singular forms such as "a," "said," and "the" used in the present disclosure and the appended claims are also intended to include multiple, unless the context clearly indicates otherwise. It is also to be understood that the term "and/or" as used herein refers to any or all possible combinations that include one or more associated listed items.

It is to be understood that although different information may be described using the terms such as "first," "second," "third," etc. in the present disclosure, the information should not be limited to these terms. These terms are used only to distinguish the same type of information from each other. For example, the first information may also be referred to as the second information without departing from the scope of the present disclosure, and similarly, the second information may also be referred to as the first information. Depending on the context, the word "if" as used herein may be interpreted as "when" or "as" or "in response to determining".

The foregoing describes specific embodiments of this specification. Other embodiments are within the scope of the appended claims. In some cases, the actions or steps described in the claims may be performed in a different order than in the embodiments and still achieve desired results. In addition, the processes depicted in the drawings do not necessarily require the specific order or sequential order shown to achieve the desired result. In certain embodiments, multitasking and parallel processing are also possible or may be advantageous.

Those skilled in the art will easily think of other embodiments of this specification after considering the specification and practicing the disclosure applied here. This disclosure is intended to cover any variations, uses, or adaptive changes of this specification, which follow the general principles of this specification and include common knowledge or customary technical means in the technical field not applied for in this specification. The specification and the embodiments are only regarded as exemplary, and the true scope and spirit of the description are pointed out by the following claims.

It should be understood that this disclosure is not limited to the precise structure that has been described above and shown in the drawings, and various modifications and changes can be made without departing from its scope. The scope of this specification is limited by the appended claims.

Some examples of the present disclosure are described above and are not intended to limit the disclosure. Any variations, equivalent replacements, modifications or the like within the spirit and principles of the present disclosure should fall within the scope of the present disclosure.

What is claimed is:

1. A method of reconstructing an image, comprising:
identifying a plurality of first scan data sets and a second scan data set from Positron Emission Tomography (PET) scan data, wherein each of the first scan data sets corresponds to an intra-crystal Compton scattering event that has occurred in a plurality of crystals of a detector and includes two or more first single photon annihilation event data groups, and each of the first single photon annihilation event data groups comprises an energy value less than a preset first energy threshold, and the second scan data set comprises one or more second single photon annihilation event data groups and each of the second single photon annihilation event data groups comprises an energy value exceed a preset second energy threshold, the preset second energy threshold being greater than the first preset energy threshold;
for each of the plurality of first scan data sets:
searching the second scan data set for a target second single photon annihilation event data group which matches with the first scan data set, and obtaining first coincidence event data from each of the first single photon annihilation event data groups in the first scan data set and the target second single photon annihilation event data group as coincidence event data recovered from an intra-crystal Compton scattering event corresponding to the first scan data set; and
reconstructing the image with the first coincidence event data and second coincidence event data which involves coincidence events corresponding to the second scan data set,
wherein the obtaining the first coincidence event data from each of the first single photon annihilation event data groups in the first scan data set and the target second single photon annihilation event data group comprises:
obtaining an initial reconstructed image by reconstructing an initial image according to scan data in the PET scan data which involves coincidence events;
performing, for each of the first single photon annihilation event data groups in the first scan data set, a coincidence processing on the first single photon annihilation event data group and the target second single photon annihilation event data group, to obtain a plurality of Lines of Response (LORs);
determining, for each of the plurality of LORs, a Time of Flight (TOF) kernel function to obtain a plurality of TOF kernel functions;
performing, for each of the plurality of TOF kernel functions, line integration with the TOF kernel function and pixel values in the initial reconstructed image to obtain a probability value of a corresponding LOR for the TOF kernel function; and
determining data comprising a first single photon annihilation event data group corresponding to a LOR of the plurality of LORs with a largest obtained probability value and the target second single photon annihilation event data group as the first coincidence event data.

2. The method according to claim 1, wherein identifying the plurality of first scan data sets and the second scan data set from the PET scan data comprises:
identifying each of the plurality of first scan data sets corresponding to the intra-crystal Compton scattering event from the PET scan data comprising:
for each single photon annihilation event data group in the PET scan data,
searching the PET scan data for a target single photon annihilation event data group which matches with the single photon annihilation event data group, wherein the target single photon annihilation event data group satisfies the following conditions:
a distance between a first spatial position indicated by spatial position information in the target single photon annihilation event data group and a second spatial position indicated by the single photon annihilation event data group is less than a preset distance threshold;
a difference between first time indicated by time information in the target single photon annihilation event data group and second time indicated by the single photon annihilation event data group is less than a preset time threshold; and
a first energy value in the target single photon annihilation event data group and a second energy value in the single photon annihilation event data group are both smaller than the first energy threshold; and
if the target single photon annihilation event data group is searched out, determining that the target single photon annihilation event data group and the single photon annihilation event data group belong to the first scan data set corresponding to the same intra-crystal Compton scattering event.

3. The method according to claim 1, wherein the PET scan data is obtained from original PET scan data by performing time walk error correction on the original PET scan data.

4. The method according to claim 3, wherein the performing the time walk error correction on the original PET scan data comprises:
obtaining, for each single photon annihilation event data group in the original PET scan data, an energy to time-walk-error correlation of a crystal corresponding to the single photon annihilation event data group with respect to a reference crystal;
obtaining a target time walk error corresponding to a target energy value in the single photon annihilation event data group based on the energy to time-walk-error correlation;
determining a sum of a time value in the single photon annihilation event data group and the target time walk error; and
updating the time value in the single photon annihilation event data group to a value of the sum.

5. The method according to claim 1, wherein the PET scan data is obtained from original PET scan data by performing system time correction on the original PET scan data.

6. A console device, comprising:
an external interface connecting a detector of a Positron Emission Tomography (PET) system, wherein the detector includes a plurality of crystals and a corresponding plurality of photoelectric converters and a processing circuit;
one or more memories storing machine-readable instructions; and
at least one processor configured to read the machine-readable instructions on the one or more memories to perform operations comprising:
identifying a plurality of first scan data sets and a second scan data set from PET scan data, wherein each of the first scan data sets corresponds to an intra-crystal Compton scattering event occurred in a plurality of crystals of a detector and includes two or more first single photon annihilation event data groups, and each of the first single photon annihilation event data groups comprises an energy value less than a preset first energy threshold, and the second scan data set comprises one or more second single photon annihilation event data groups and each of the second single photon annihilation event data groups comprises an energy value exceed a preset second energy threshold, the preset second energy threshold being greater than the first preset energy threshold;

for each of the plurality of first scan data sets: searching the second scan data set for a target second single photon annihilation event data group which matches with the first scan data set, and obtaining first coincidence event data from each of the first single photon annihilation event data groups in the first scan data set and the target second single photon annihilation event data group as coincidence event data recovered from an intra-crystal Compton scattering event corresponding to the first scan data set; reconstructing an image with the first coincidence event data and second coincidence event data which involves coincidence events corresponding to the second scan data set;

wherein the obtaining the first coincidence event data from each of the first single photon annihilation event data groups in the first scan data set and the target second single photon annihilation event data group comprises:

obtaining an initial reconstructed image by reconstructing an image according to scan data in the PET scan data which involves coincidence events;

performing, for each of the first single photon annihilation event data groups in the first scan data set, a coincidence processing on the first single photon annihilation event data group and the target second single photon annihilation event data group, to obtain a plurality of Lines of Response (LORs);

determining, for each of plurality of the LORs, a Time of Flight (TOF) kernel function to obtain a plurality of TOF kernel functions; performing, for each of the plurality of TOF kernel functions, line integration with the TOF kernel function and pixel values in the initial reconstructed image to obtain a probability value of a corresponding LOR for the TOF kernel function;

determining data comprising a first single photon annihilation event data group corresponding to a LOR of the plurality of LORs with a largest obtained probability value and the target second single photon annihilation event data group as the first coincidence event data;

and an internal bus connecting the external interface, the at least one processor and the one or more memories.

7. The device according to claim 6, wherein the at least one processor is configured to perform:

for each single photon annihilation event data group in the PET scan data, searching the PET scan data for a target single photon annihilation event data group which matches with the single photon annihilation event data group, wherein the target single photon annihilation event data group satisfies the following conditions:

a distance between a first spatial position indicated by spatial position information in the target single photon annihilation event data group and a second spatial position indicated by the single photon annihilation event data group is less than a preset distance threshold;

a difference between first time indicated by time information in the target single photon annihilation event data group and second time indicated by the single photon annihilation event data group is less than a preset time threshold; and a first energy value in the target single photon annihilation event data group and a second energy value in the single photon annihilation event data group are both smaller than the first energy threshold; and if the target single photon annihilation event data group is searched out, determining that the target single photon annihilation event data group and the single photon annihilation event data group belong to a first scan data set corresponding to the intra-crystal Compton scattering event.

8. The device according to claim 6, wherein the PET scan data is obtained from original PET scan data by performing time walk error correction on the original PET scan data.

9. The device according to claim 8, wherein the at least one processor is configured to perform:

obtaining, for each single photon annihilation event data group in the original PET scan data, an energy to time-walk-error correlation of a crystal corresponding to the single photon annihilation event data group with respect to a reference crystal;

obtaining a target time walk error corresponding to a target energy value in the single photon annihilation event data group based on the energy to time-walk-error correlation;

determining a sum of a time value in the single photon annihilation event data group and the target time walk error; and updating the time value in the single photon annihilation event data group to a value of the sum.

10. The device according to claim 6, wherein the PET scan data is obtained from original PET scan data by performing system time correction on the original PET scan data.

11. A Positron Emission Tomography (PET) system, comprising:

a scanning bed;

a detector, wherein the detector comprises:

a plurality of crystals, wherein the crystals are configured to detect a high-energy photon emitted from an inside of a subject and convert the high-energy photon into an optical signal during a scanning process of the PET system;

a corresponding plurality of photoelectric converters, wherein the photoelectric converters are configured to convert the optical signal into an electrical signal; and a processing circuit for converting the electrical signal into a pulse signal and collecting energy information of the pulse signal; and a console device, comprising:

an external interface connecting the detector;

one or more memories storing machine readable instructions; and at least one processor configured to read the machine readable instructions on the one or more memories to perform operations comprising:

identifying a plurality of first scan data sets and a second scan data set from PET scan data, wherein each of the first scan data sets corresponds to an intra-crystal Compton scattering event occurred in a plurality of crystals of a detector and includes two or more first single photon annihilation event data groups, and each of the first single photon annihilation event data groups comprises an energy value less than a preset first energy threshold, and the second scan data set comprises one or more second single photon annihilation event data groups and each of the second single photon annihilation event data groups comprises an energy value exceed a preset second energy threshold, the preset second energy threshold being greater than the first preset energy threshold;

for each of the plurality of first scan data sets:
searching the second scan data set for a target second single photon annihilation event data group which matches with the first scan data set, and obtaining first coincidence event data from each of the first single photon annihilation event data groups in the first scan data set and the target second single photon annihilation event data group as coincidence event data recovered from an intra-crystal Compton scattering event corresponding to the first scan data set; and reconstructing an image with the first coincidence event data and second coincidence event data which involves coincidence events corresponding to the second scan data set;

wherein the obtaining the first coincidence event data from each of the first single photon annihilation event data groups in the first scan data set and the target second single photon annihilation event data group comprises:

obtaining an initial reconstructed image by reconstructing an image according to scan data in the PET scan data which involves coincidence events;

performing, for each of the first single photon annihilation event data groups in the first scan data set, a coincidence processing on the first single photon annihilation event data group and the target second single photon annihilation event data group, to obtain a plurality of Lines of Response (LORs);

determining, for each of the plurality of LORs, a Time of Flight (TOF) kernel function to obtain a plurality of TOF kernel functions;

performing, for each of the plurality of TOF kernel functions, line integration with the TOF kernel function and pixel values in the initial reconstructed image to obtain a probability value of a corresponding LOR for the TOF kernel function; and determining data comprising a first single photon annihilation event data group corresponding to a LOR of the plurality of LORs with a largest obtained probability value and the target second single photon annihilation event data group as the first coincidence event data.

12. The system according to claim 11, wherein the console device is configured to perform:

for each single photon annihilation event data group in the PET scan data, searching the PET scan data for a target single photon annihilation event data group which matches with the single photon annihilation event data group, wherein the target single photon annihilation event data group satisfies the following conditions:

a distance between a first spatial position indicated by spatial position information in the target single photon annihilation event data group and a second spatial position indicated by the single photon annihilation event data group is less than a preset distance threshold;

a difference between first time indicated by time information in the target single photon annihilation event data group and second time indicated by the single photon annihilation event data group is less than a preset time threshold; and a first energy value in the target single photon annihilation event data group and a second energy value in the single photon annihilation event data group are both smaller than the first energy threshold; and if the target single photon annihilation event data group is searched out, determining that the target single photon annihilation event data group and the single photon annihilation event data group belong to a first scan data set corresponding to the same intra-crystal Compton scattering event.

13. The system according to claim 11, wherein the PET scan data is obtained from original PET scan data by performing time walk error correction on the original PET scan data.

14. The system according to claim 13, wherein the console device is configured to perform:

obtaining, for each single photon annihilation event data group in the original PET scan data, an energy to time-walk-error correlation of a crystal corresponding to the single photon annihilation event data group with respect to a reference crystal;

obtaining a target time walk error corresponding to a target energy value in the single photon annihilation event data group based on the energy to time-walk-error correlation;

determining a sum of a time value in the single photon annihilation event data group and the target time walk error; and updating the time value in the single photon annihilation event data group to a value of the sum.

15. The system according to claim 11, wherein the PET scan data is obtained from original PET scan data by performing system time correction on the original PET scan data.

16. A non-transitory computer-readable storage medium storing programming instructions for execution by at least one processor to perform operations comprising:

identifying a plurality of first scan data sets and a second scan data set from Positron Emission Tomography (PET) scan data, wherein each of the first scan data sets corresponds to an intra-crystal Compton scattering event occurred in a plurality of crystals of a detector and includes two or more first single photon annihilation event data groups, and each of the first single photon annihilation event data groups comprises an energy value less than a preset first energy threshold, and the second scan data set comprises one or more second single photon annihilation event data groups and each of the second single photon annihilation event data groups comprises an energy value exceed a preset second energy threshold, the preset second energy threshold being greater than the first preset energy threshold;

for each of the plurality of first scan data sets:
searching the second scan data set for a target second single photon annihilation event data group which matches with the first scan data set, and obtaining first coincidence event data from each of the first single photon annihilation event data groups in the first scan data set and the target second single photon annihilation event data group as coincidence event data recovered from an intra-crystal Compton scattering event corresponding to the first scan data set; and reconstructing an image with the first coincidence event data and second coincidence event data which involves coincidence events corresponding to the second scan data set;

wherein the obtaining the first coincidence event data from each of the first single photon annihilation event data groups in the first scan data set and the target second single photon annihilation event data group comprises:

obtaining an initial reconstructed image by reconstructing an initial image according to scan data in the PET scan data which involves coincidence events;

performing, for each of the first single photon annihilation event data groups in the first scan data set, a coincidence processing on the first single photon annihilation event data group and the target second single photon annihilation event data group, to obtain a plurality of Lines of Response (LORs);

determining, for each of the plurality of LORs, a Time of Flight (TOF) kernel function to obtain a plurality of TOF kernel functions;

performing, for each of the plurality of TOF kernel functions, line integration with the TOF kernel function and pixel values in the initial reconstructed image to obtain a probability value of a corresponding LOR for the TOF kernel function; and determining data comprising a first single photon annihilation event data group corresponding to a LOR of the plurality of LORs with a largest obtained probability value and the target second single photon annihilation event data group as the first coincidence event data.

* * * * *